United States Patent [19]

Samuelson et al.

[11] Patent Number: 5,611,802
[45] Date of Patent: Mar. 18, 1997

[54] METHOD AND APPARATUS FOR RESECTING BONE

[76] Inventors: Kent M. Samuelson, 370 Ninth Ave., Salt Lake City, Utah 84103; Mark V. Vandewalle, 7401 E. Shoop Rd., Pierceton, Ind. 46562

[21] Appl. No.: 389,136

[22] Filed: Feb. 14, 1995

[51] Int. Cl.⁶ .............................. A61F 5/00; A61B 17/58
[52] U.S. Cl. .................. 606/86; 606/87; 606/88
[58] Field of Search .................... 606/79, 82, 86, 606/87, 88, 89, 96, 97, 98

[56] References Cited

U.S. PATENT DOCUMENTS

| | | | |
|---|---|---|---|
| 4,722,330 | 2/1988 | Russell et al. | 606/88 |
| 4,759,350 | 7/1988 | Dunn et al. . | |
| 4,952,213 | 8/1990 | Bowman et al. | 606/88 |
| 5,147,365 | 9/1992 | Whitlock et al. | 606/92 |
| 5,364,401 | 11/1994 | Ferrante et al. | 606/88 |
| 5,415,663 | 5/1995 | Luckman et al. . | |
| 5,445,640 | 8/1995 | Johnson et al. | 606/87 |

OTHER PUBLICATIONS

Intermedics Orthopedics brochure entitled "The Intermedics Natural–Knee System", having a copyright date of 1986, by Aaron A. Hofmann.

Protek brochure entitled "Mark II – Total Knee Replacement System", pre–Feb. 19, 1993.

J & J Patellar Cutting Guide Model No. 88–5034, pre–Feb. 1995.

Primary Examiner—Michael Powell Buiz
Assistant Examiner—Mark S. Leonardo
Attorney, Agent, or Firm—Harness, Dickey & Pierce, P.L.C.

[57] ABSTRACT

A method and apparatus for resecting bone includes an anterior femur resection guide assembly for performing an anterior femur osteotomy, a distal femur resecting guide assembly for performing a distal femur osteotomy, a compound posterior femur-chamfer resection guide assembly for performing an anterior femur osteotomy, and a tibia resection guide assembly for performing a proximal tibia osteotomy. The anterior femur resection guide assembly, the distal femur resecting guide assembly, the tibia resecting guide assembly, and the compound posterior femur-chamfer resection guide assembly each includes a capture plate subassembly which restricts lateral movement of a saw during resection. The distal femur resecting guide assembly and the tibia resecting guide assembly also include subassemblies for verifying the correct positioning of a distal femur and proximal tibia osteotomies.

11 Claims, 8 Drawing Sheets

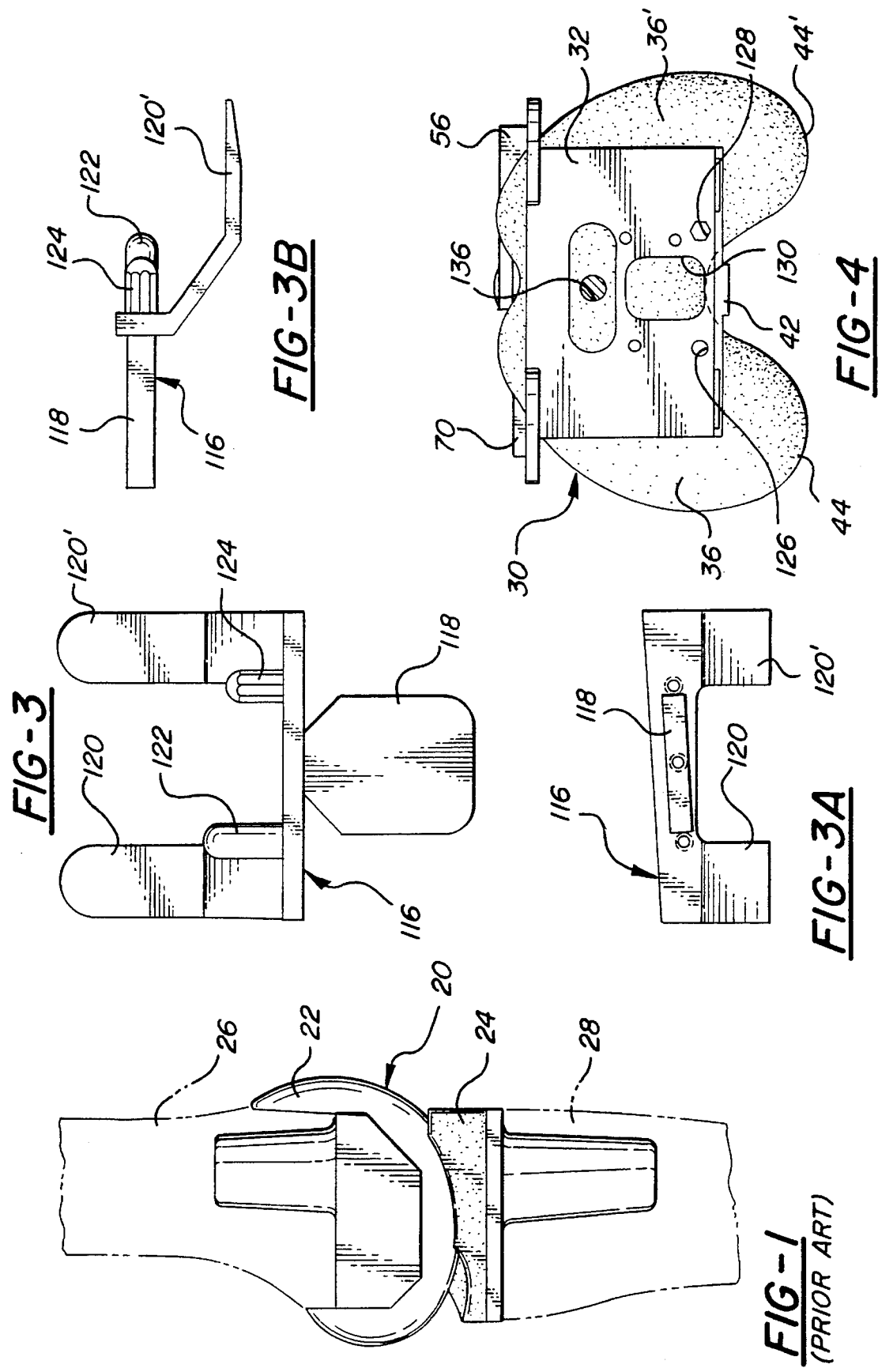

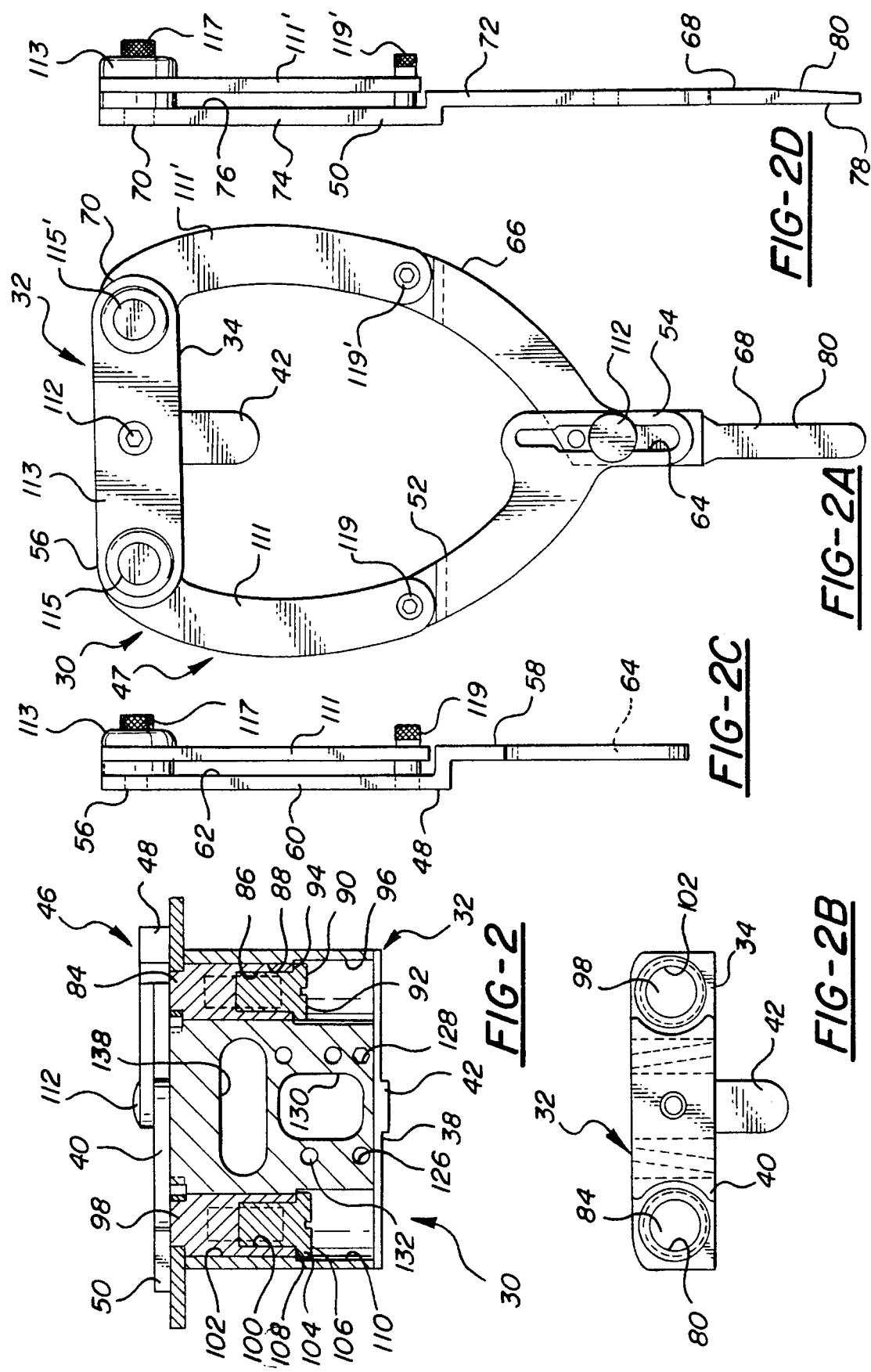

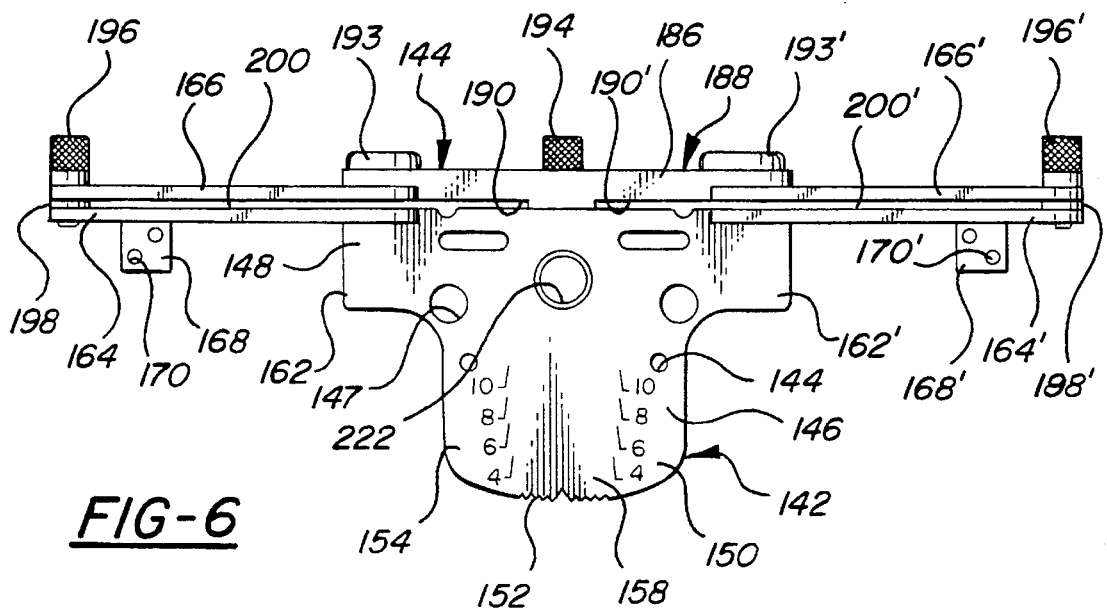
FIG-6
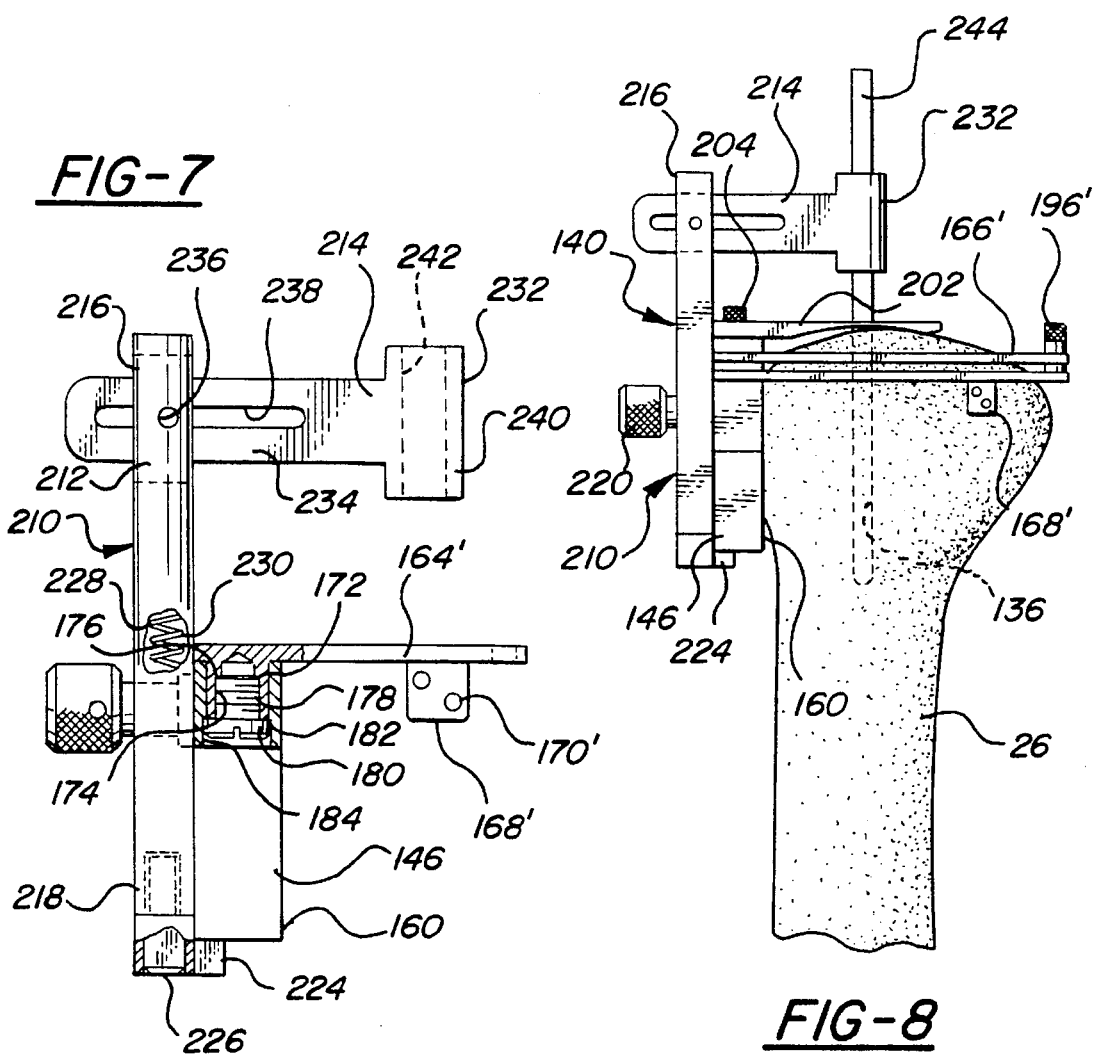
FIG-7
FIG-8

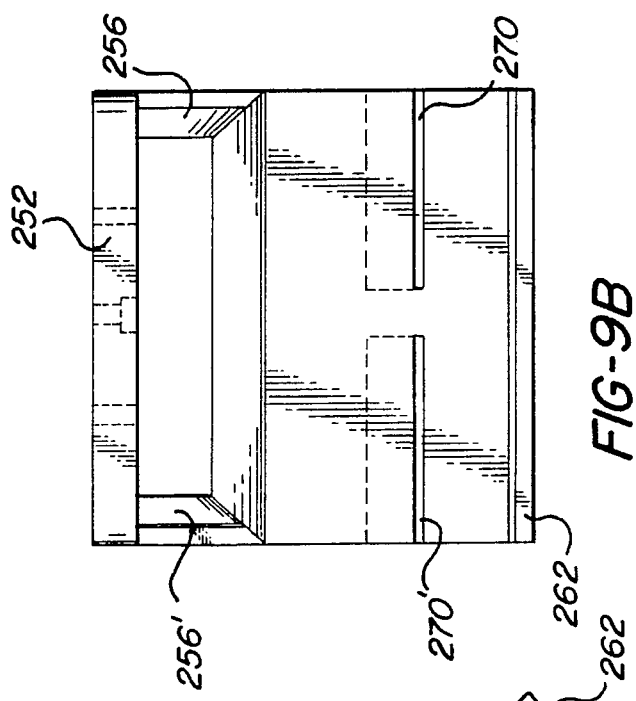
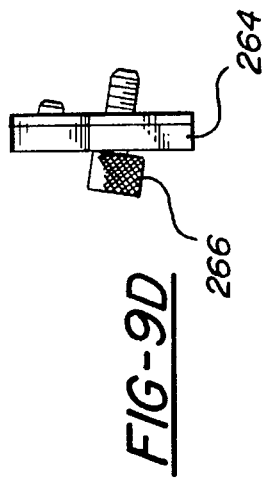
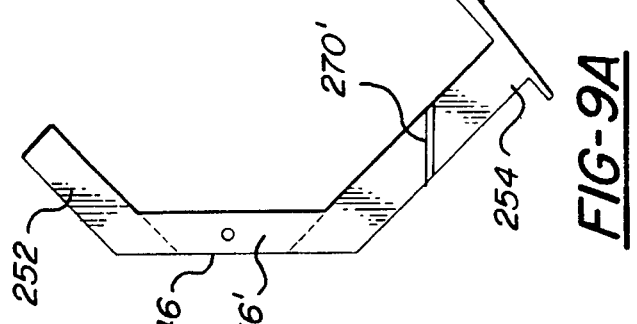
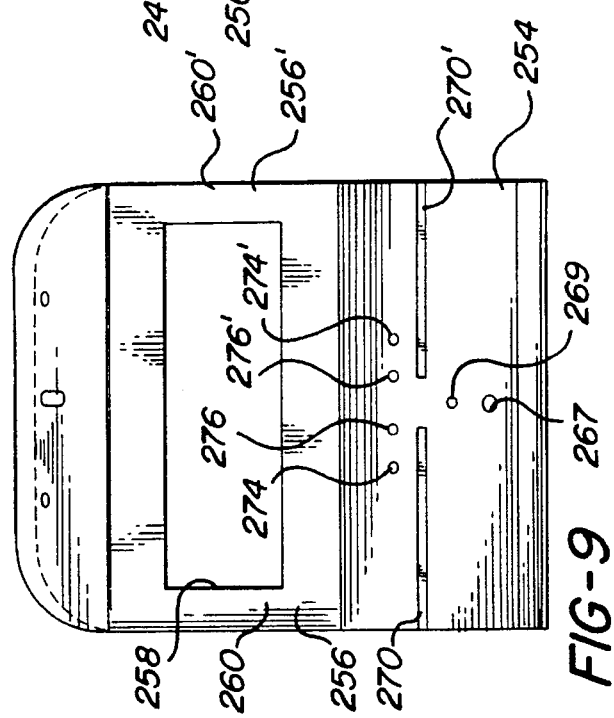
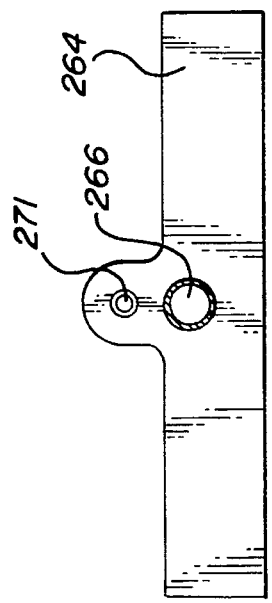

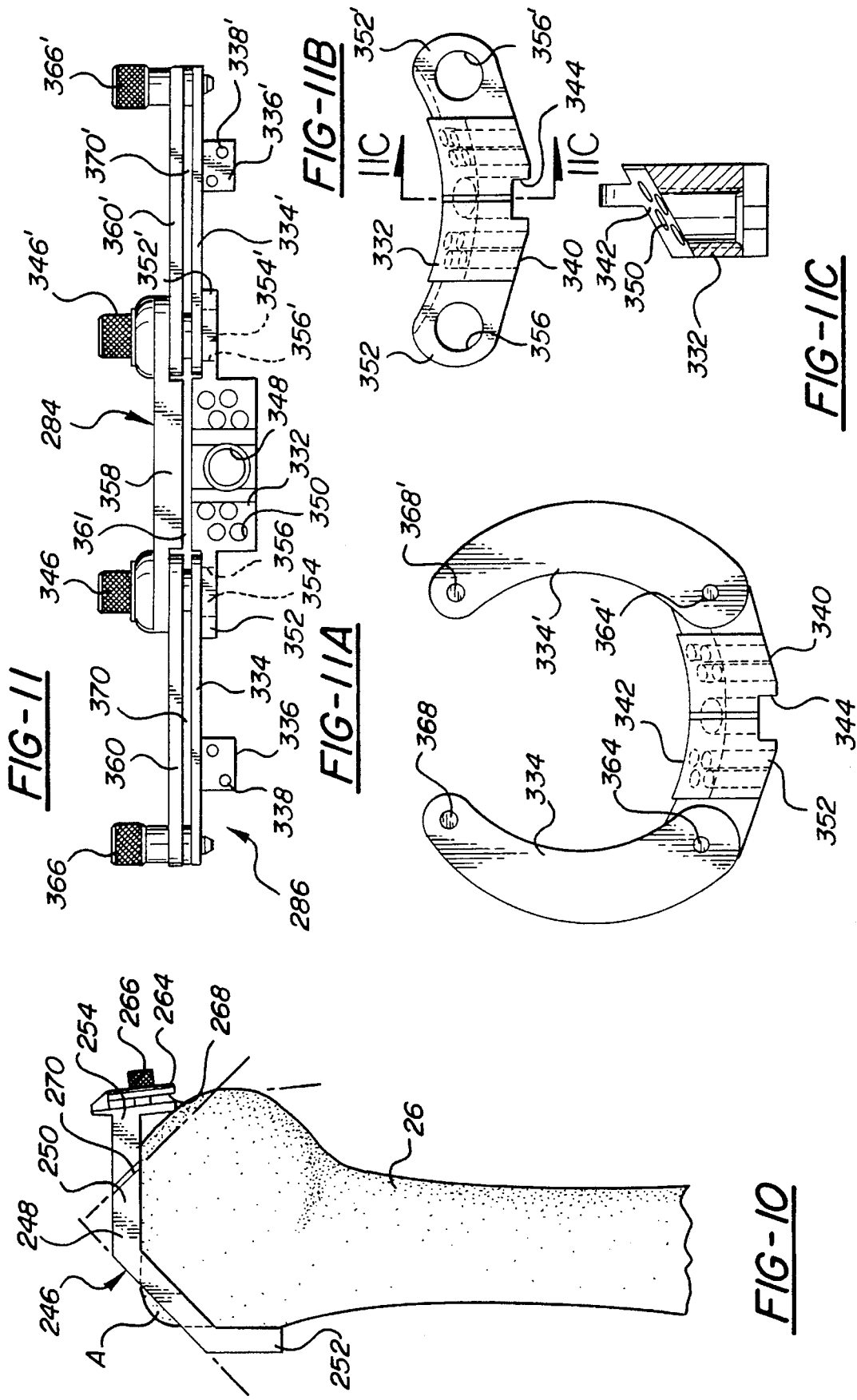

METHOD AND APPARATUS FOR RESECTING BONE

BACKGROUND OF THE INVENTION

The present invention relates generally to a method and apparatus for resecting a long bone, and more particularly, to a method and apparatus for preparing the distal end of the femur and the proximal end of the tibia to receive a prosthetic knee joint.

A natural joint in the human body such as a knee joint may undergo degenerative changes due to a variety of etiologies. When these degenerative changes become advanced and are irreversible, it may ultimately become necessary to replace the natural joint with a prosthetic joint. Such a prosthetic joint often includes several biocompatible components which are formed from high strength synthetic materials. These materials are not only able to accommodate the various loading conditions that the prosthetic joint may encounter, but are also biocompatible with the human body.

The effective reinstatement of natural joint functioning through use of a joint prosthesis depends on the combined influences of component features and accurate anatomical positioning of the components. The positioning factor makes the instruments, and their sequence of application, keys to achieving natural joint functioning. The instruments aid in the making of proper cuts of the appropriate portions of the bones in preparation of receiving the prosthetic joint components and also have utility in correctly aligning the angle of the cuts relative to the bone.

Initially, it is necessary that the distal end of the femur be appropriately cut so as to receive the prosthetic femoral component. According to one approach for resecting the distal end of the femur, the anterior surface of the distal end of the femur is first resected. Once the anterior surface is resected, the distal femur osteotomy is performed. Thereafter, the posterior femoral osteotomy is made to resect the posterior surface of the femur. Chamfer cuts are next made intersecting both the flat surfaces of the distal femur and the anterior femur and the flat surfaces of the distal femur and the posterior femur. Once the anterior, posterior, and distal osteotomies and the chamfer cuts are made, the distal end of the femur is reamed to receive the biocompatible femoral component of the prosthetic joint.

Similarly, the proximal end of the tibia must also be prepared to receive a biocompatible component. A proximal tibia osteotomy is undertaken to resect the proximal tibial surface. Axial reaming is also required to prepare the distal end of the tibia to receive a biocompatible tibial component.

The surgical steps necessary to prepare the distal end of the femur and the proximal end of the tibia for receiving their respective prosthetic components are inherently complex. The procedures are made complex by the fact that careful attention must be paid to the amount of bone being resected, the angles of the cut with respect to each other, and the angles of the cut with respect to the axes of both the femur and the tibia. If either the femoral or the tibial component fail to fit properly, revision surgery may ultimately be necessary.

The proper execution of the resection is the most important aspect in the preparation of a long bone for receiving a prosthetic component. There are many known devices which provide a guide surface for the cutting blade and these devices are typically attached to or positioned in alignment with the bone. The basic forms of these devices include "armless" and "armed" guides. Both forms include a body having a blade-positioning surface. The body is typically a flat-sided block having a flat surface that acts as a saw guide. The body is temporarily attached to the bone during resection. Some variations of the typical block-shaped bodies include bodies having curved walls that wrap partially around the bone. In the "armed" version of known saw guides, a pair of saw guide arms are pivotably and permanently attached to the saw-guide body and partially wrap around the bone.

However, these designs fail to provide a satisfactory guide for resection. Specifically, and with respect to the "armless" devices, these devices typically only provide a small blade-positioning surface, and fail to provide a surface that offers more than 20 or 30 degrees of support around the bone, even where the body is curved. While providing a larger blade-positioning surface, in the "armed" form of the device the arms are pivotably attached to the body in a permanent manner. The arms are formed having the widest possible curvature in an effort by the manufacturer to provide a "universal" saw guide capable of fitting around a bone having a large diameter. The "universal" design allows the saw guide, in theory, to be applied to bones of lesser diameters as well. However, this "one size fits all" construction fails to provide a reliable cutting surface when designed to allow for the largest possible bone to be resected. This is so because the saw blades, which are often only about two inches long and are required to make cuts of about one-and-a-half inches, are not properly supported by a blade-positioning surface that may be positioned some distance from the bone surface. Ideally, the operator would be able to maintain the cut guide in close proximity to the bone to provide support for the blade and to thereby reduce the incidence of improper cuts, blade deflection, and scything. The failure of "one size fits all" guides becomes increasingly acute as the device is applied to bones of decreasing diameters.

Another difficulty encountered by surgeons in the execution of resection is blade control. Many known cutting guide devices provide only limited assistance to the surgeon in controlling movement of the blade. Specifically, the surgeon must reciprocate the blade against the blade-positioning surface while trying to prevent the blade from being lifted off of the surface during cutting. In an effort to overcome this, some guides have incorporated saw blade capture plates that are positioned spaced apart from the saw guide surface, this spacing forming a saw guide slot, the slot being desirable to reduce scything. Hitherto these slots have only been provided on the "armless" saw guides, and, while limiting lateral movement of the saw blade to a certain extent, suffer from the same limited blade-positioning surface of these types of devices.

Accordingly, it is desired to provide a system which allows relatively uncomplicated preparation and resecting of the bone surfaces for adaptation to receive biocompatible components of a knee joint prosthesis.

SUMMARY OF THE INVENTION

Generally, the present invention provides a method and apparatus for resecting any long bone in preparation for receiving a prosthetic component. Particularly, the present invention is directed to an apparatus for resecting a knee joint in preparation for receiving a prosthetic knee which provides minimal complexity for the surgeon while providing maximum accuracy in the form of saw blade control for receiving the respective prosthetic components. The invention encompasses a reliable and efficient method for preparing both the distal femur and the proximal tibia for a knee joint prosthesis.

More specifically, the method and apparatus for resecting bone according to the present invention includes an anterior femur resection guide assembly for performing an anterior femur osteotomy, a distal femur resecting guide assembly for performing a distal femur osteotomy, and a compound posterior femur-chamfer resection guide assembly for performing an anterior femur osteotomy as well as chamfer cuts between the resected anterior and distal surfaces and the resected posterior and distal surfaces. The apparatus of the present invention further includes a tibia resection guide assembly for performing a proximal tibia osteotomy.

The anterior femur resection guide assembly, the distal femur resecting guide assembly, the tibia resection guide assembly, and the compound posterior femur-chamfer resection guide assembly each includes saw guide bodies having pivotably attached arms. Both the saw guide bodies and the pivotably attached arms include capture plate components which restrict lateral movement of a saw during resection.

Furthermore, the anterior femur resection guide assembly, the distal femur resecting guide assembly, and the tibia resection guide assembly each includes interchangeable arms having different lengths and degrees of curvature that find application for use with bones of different diameters, thus being able to "personalize" these subassemblies for each patient.

The distal femur resecting guide assembly and the tibia resection guide assembly also includes subassemblies for verifying the correct positioning of the distal femur and proximal tibia osteotomies.

An advantage of the present invention is to provide a saw guide having interchangeable arms of different sizes that provide a blade-positioning surface that surrounds long bones of a variety of diameters.

A further advantage of the present invention is to provide such a saw guide that includes saw blade capture components on the saw guide body as well as the saw guide positioning arms.

An additional advantage of the present invention is to provide a method for resecting bone in preparation of the distal end of the femur and a proximal end of the tibia for receipt of a knee joint prosthesis which requires a minimal number of steps.

Yet another advantage of the present invention is to provide such an apparatus that includes adjustable components to accommodate bones of different sizes.

Another advantage of the present invention is to provide a method and apparatus for resecting a bone which is easy to use and accurately determines where the tibial and femoral cuts should be made.

A further advantage of the present invention is to provide a method and apparatus for preparing a knee joint for a knee joint prosthesis which correctly and reliably positions the cut with respect to the bone so as to accurately create the correct surfaces necessary for proper fitting of the prosthetic components.

Another advantage of the present invention is to provide an apparatus for resecting a bone which provides a guide against which a saw blade may be positioned.

A further advantage of the present invention is to provide an apparatus for resecting bone which includes a system of capturing a saw blade so as to reduce the likelihood of the blade being lifted off of the saw guide cutting surface during the cutting operation.

BRIEF DESCRIPTION OF THE DRAWINGS

The various advantages of the present invention will become apparent to one skilled in the art by reading the following specification and subjoined claims and by referencing the following drawings in which:

FIG. 1 is a sagittal view of a left knee joint having a knee joint prosthesis, with the tibia and the femur of the natural knee shown in phantom;

FIG. 2 is a front view of the anterior femoral resection guide assembly according to the present invention;

FIG. 2A is an end view of the anterior femoral resection guide assembly of FIG. 2;

FIG. 2B is similar to the view of FIG. 2A but without the saw guide arms;

FIG. 2C is a side view of the upper swing arm with a capture arm illustrated in FIG. 2A;

FIG. 2D is a side view of the lower swing with a capture arm illustrated in FIG. 2A;

FIG. 3 is a plan view of the posterior condyle sled for use with the anterior femoral resection guide assembly of the present invention;

FIG. 3A is an end view of the condyle sled of FIG. 3;

FIG. 3B is a side view of the condyle sled of FIG. 3;

FIG. 4 is an end view of a distal femur showing the anterior femoral resecting guide assembly in place;

FIG. 6 is an elevated side view of the saw guide subassembly and the attached capture plate subassembly of the distal femoral resection guide assembly according to the present invention;

FIG. 7 is an end view of the distal femoral resection guide assembly of FIG. 6 showing the valgus guide subassembly in position, attached to the saw guide subassembly;

FIG. 8 is a side view of the distal femoral resection guide assembly including the valgus guide subassembly of FIG. 7 and an intramedullary rod in place on the distal end of a femur;

FIG. 9 is a top plan view of the chamfer guide according to the present invention;

FIG. 9A is a side view of the guide of FIG. 9;

FIG. 9B is a bottom view of the chamfer guide of FIG. 9;

FIG. 9C is a top plan view of the capture plate for use with the chamfer guide of FIG. 9;

FIG. 9D is an end view of the capture plate of FIG. 9C;

FIG. 10 is a side view of the chamfer guide of the present invention in place on the distal end of a femur;

FIG. 11 is an elevated side view of the saw guide subassembly and the attached capture plate subassembly of the tibia resection guide assembly according to the present invention;

FIG. 11A is a top plan view of the saw guide subassembly of the tibia resection guide assembly FIG. 11 without the capture plate subassembly;

FIG. 11B is a view similar to that of FIG. 11A but illustrating only the block of the saw guide subassembly;

FIG. 11C is a view taken along lines 11C—11C of FIG. 11B;

DETAILED DESCRIPTION OF THE PREFERRED EMBODIMENTS

Figure 6A:
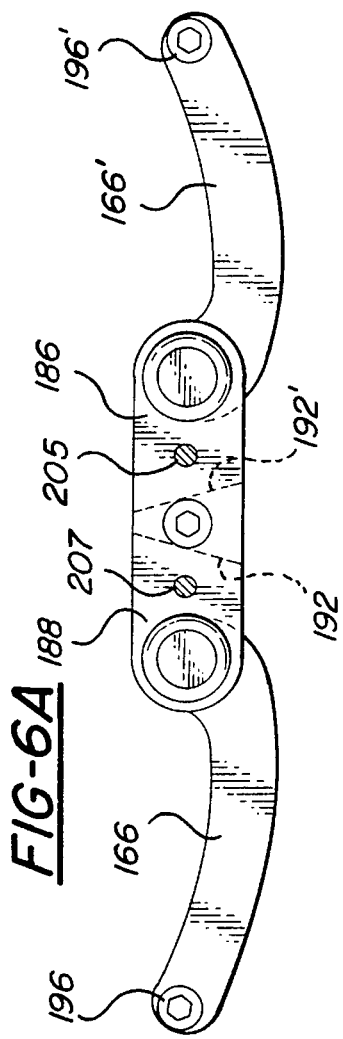
FIG. 6A is a top plan view of the capture plate subassembly of the distal femoral resection guide assembly of FIG. 6.
Figure 6B:
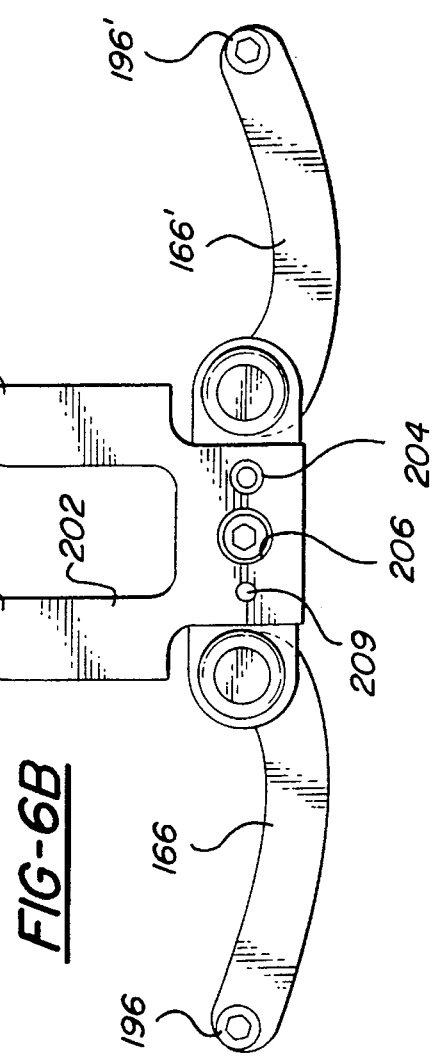
FIG. 6B is a view similar to that of 6A but illustrating the condyle positioning shoe in place on the top of the guide assembly.

It should be understood that while this invention is described in connection with a particular example thereof, the scope of the invention may not be so limited. Rather, those skilled in the art will appreciate that the following teachings can be used in a much wider variety of applications than the examples specifically mentioned herein.

Referring to FIG. 1, there is shown a knee joint prosthesis 20 having a femoral component 22 and a tibial component 24. While the invention is directed to the resection of the tibia and the femur, it must be understood that the invention may find application in any long bone requiring resection.

The femoral component 22 and the tibial component 24 are shown secured to a femur 26 and a tibia 28 respectively of a surgically resected right knee joint, with the femur 26 and the tibia 28 being shown in phantom. It will be understood that any suitable knee joint prosthesis may be utilized in the present invention. It will be similarly understood that while the left knee joint prosthesis 20 is shown, the present invention may be used for both right and left knee joint prosthetic surgery.

Fitting of the knee joint prosthesis 20 is possible after appropriate resections have been made to the femur 26 and the tibia 28. Specifically, six resections in all are made, five to the distal end of the femur 26 and one to the proximal end of the tibia 28. The five resections to the distal end of the femur 26 include anterior and posterior femur osteotomies, the distal femur osteotomy, and chamfer cuts between the resected anterior and distal surfaces and between the resected posterior and distal surfaces.

Figure 5:
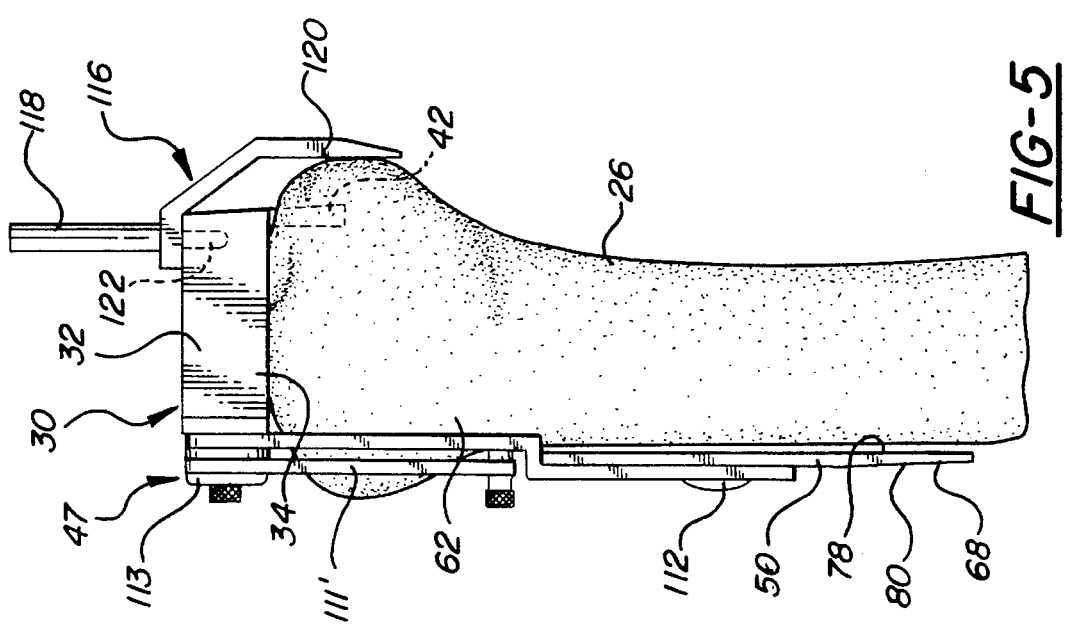
FIG. 5 is a side view of the distal femur of FIG. 4 illustrating the anterior femoral resecting guide assembly and the posterior condyle sled in position.

The initial resection to the femur 26 is the anterior femur osteotomy. An anterior resection guide assembly, generally illustrated as 30 in FIGS. 2, 2A, 2B, 2C, 2D, 4 and 5, is provided to perform this resection. The guide assembly 30 includes a guide block 32 having a generally rectangular shape. The block 32 includes an inner flat surface 34 which, when in position for performing a resection, rests against the distal condyles 36 and 36', as illustrated in FIG. 5.

The block 32 includes a posterior side 38 and an anterior side 40. Fitted to the posterior side 38 and extending away from the flat surface 34 is a centering tab 42. By positioning the tab 42 between the posterior condyles 44 and 44' (as shown in FIG. 4), the surgeon can properly center the assembly 30 on the distal end of the femur 26.

Fitted to the anterior side 40 of the block 32 are a saw guide subassembly 46 and a capture subassembly 47, the latter best being shown in FIGS. 2A and 5. The subassembly 46 comprises an upper arm 48 and a lower arm 50. The upper arm 48 comprises an arcuate portion 52 and a straight portion 54. The arcuate portion 52 includes an attaching end 56, a raised portion 58, and a recessed portion 60. As best seen in FIG. 2C, the raised portion 58 is offset with respect to the recessed portion 60. The recessed portion 60 includes a saw guide cutting surface 62. The straight portion 54 includes an axially defined elongated slot 64.

The lower arm 50 also comprises an arcuate portion 66 and a straight portion 68. The arcuate portion 66 includes an attaching end 70. The arcuate portion 66 further includes a raised portion 72 and a recessed portion 74, the portions 72 and 74 being offset with respect to each other. The recessed portion 74 includes a saw guide surface 76. The saw guide cutting surfaces 62 and 76 are coplanar. The straight portion 68 has an anterior-cortex positioning side 78 and further has a smooth taper 80 that slopes away from the straight portion 68. This arrangement holds the upper arm 48 to the lower arm 50 to form the subassembly 46.

A cylinder 84 is fixed to the attaching end 56 of the upper arm 48 and includes a threaded blind bore 86. The cylinder 84 is rotatably mounted in a throughbore 88 formed in the block 32. A fastener 90 is threaded into the threaded bore 86. The fastener 90 includes a head 92 that rotatably rests against a shoulder 94 formed by a counterbore 96 that is coaxial with the throughbore 88.

In the same manner, a cylinder 98 is fixed to the attaching end 70 of the lower arm 50 and includes a threaded blind bore 100. The cylinder 98 is rotatably mounted in a throughbore 102 formed in the block 32. A fastener 104 is threaded into the threaded bore 100. The fastener 104 includes a head 106 that rotatably rests against a shoulder 108 formed by a counterbore 110 that is coaxial with the throughbore 102.

The capture subassembly 47 includes a pair of capture arms 111 and 111' which are mirror images of each other and a center plate 113. The arms 111 and 111' are pivotably attached to the center plate 113 by a pair of fasteners 115 and 115'. The arms 111 and 111' respectively overlap the arms 48 and 50, but are in spaced-apart relation therefrom, thus defining saw blade slots therebetween as illustrated in FIGS. 2C, 2D and 5. The subassembly 47 is removable as a single component from the subassembly 46. A center capture bolt 117 releasably holds the center plate 113 to the block 32 while arm capture bolts 119 and 119' releasably hold the arms 111 and 111' to the arms 48 and 50 respectively. When the subassembly 47 is in place, the arm 111 is pivotable with the arm 48 and the arm 111' is pivotable with the arm 50.

The subassembly 47 is normally in its attached position as illustrated in FIGS. 2A and 5 during and between surgeries and would ordinarily be removed only for cleaning or for maintenance. The arms 111 and 111' as well as the arms 48 and 50 are provided in different sizes to accommodate femurs of different diameters.

By the above-described arrangements, the attaching end 56 of the upper arm 48 is pivotably attached to the block 32 and the attaching end 70 of the lower arm 50 is also pivotably attached to the block 32. A fastener 112 is fixed to the upper arm 48 through the slot 64. With the arms 48 and 50 attached in this manner to the block 32 and with the overlapping arms 111 and 111' arms attached to the center plate 113, the attached subassemblies 46 and 47 are capable of a simultaneous swinging motion with respect to the block 32 and the center plate 113 as is required for adjusting the assembly 30 for a proper fit. As may be seen with respect to FIG. 5, when the assembly 30 is in its resecting position, the swing arm subassembly 46 and its attached subassembly 47 are positioned at a 90 degree angle with respect to the block 32.

A posterior condyle sled 116, best illustrated in FIGS. 3, 3A, and 3B, is provided to allow accurate positioning of the assembly guide 30 on the distal end of the femur 26 prior to cutting. The sled 116 is removably attachable to the assembly 30 and includes a positioning tab 118 and a pair of posterior condyle feet 120 and 120'. The sled 116 further includes a round dowel 122 and a diamond dowel 124 projecting from the body 118. The round dowel 122 mates with a round aperture 126 formed in the block 32. Similarly, the diamond dowel 124 mates with a diamond aperture 128 also formed in the block 32. This arrangement assures correct attachment of the sled 116 to the block 32. The positioning tab 118 is provided for the surgeon to grasp the sled 116 while attaching it to before removing it from the guide assembly 30.

The anterior resection of the femur 26 is made as follows using the present invention. The surgeon first guides the taper 80 of the arm 50 along the anterior cortex of the femur 26 away from the distal end of the femur 26 between the muscle tissue and the bone. Because of the provision of the taper 80, it is not necessary to make an excessive axial incision through the tissue of the leg, and an incision merely proximal to the condyles is all that is necessary. Axial movement of the taper 80 is halted when the flat surface 34 of the block 32 abuts the femur 26. The arms 48 and 50 are wrapped around the anterior portion of the distal condyles 36 and 36'.

Alignment of the assembly 30 is made by initially positioning the flat surface 34 of the block 32 against the distal condyles 36 and 36'. The surgeon then looks through a window 130 formed in the block 32 to center the block 32 by observing the position of the block 32 with respect to the axis of the intercondylar notch and then adjusting the block 32 until the notch appears in the center of the window 130. Correct centering of the block 32 on the distal end of the femur 26 is also assured by positioning the centering tab 42 between the posterior condyles 44 and 44' as best illustrated in FIG. 4. This feature limits medial-lateral movement of the block 32. The posterior condyle sled 116 is then attached to the block 32 such that the condyle foot 120 rests against the posterior condyle 44 and the condyle foot 120' rests against the posterior condyle 44'. The correct inserted position of the sled 116 is illustrated in FIG. 5. This feature, combined with the swing arm subassembly 46, limits anterior-posterior movement of the block 32. With the block 32 in its preferred position, retaining pins or screws (not shown) are temporarily fitted through at least two of holes 132 formed in the block 32.

With the assembly 30 thus fixed in its correct position, the anterior osteotomy of the distal end of the femur 26 can be performed. The saw guide surface 62 of the upper arm 48 and the saw guide surface 76 of the lower arm 50 jointly provide a common, coplanar surface against which a bone saw (not shown) is positioned to cut through the protruding anterior bone portion 134 as shown in FIG. 5.

In addition to providing a guide for performing the anterior osteotomy, the assembly 30 allows the surgeon to form an axial intramedullary rod hole 136 in the distal end of the femur 26. This is done by a bayonet bit (not shown) driven by a drill motor being inserted through an elongated medial-lateral drill slot 138 formed in the block 32. The surgeon directs the drill motor so that the axis of the bayonet bit is somewhat offset with respect to the long axis of the femur 26. After the hole 136 is started, the surgeon straightens the drill so that the bit is aligned with the axis of the femur 26 and proceeds to deepen the hole 136. After the anterior cut is made and the axial intramedullary rod hole 136 is formed, the sled 116 is removed from the block 32 and the assembly 30 is removed from the distal end of the femur 26.

The distal end of the femur 26 is thus ready for the distal resection. To this end, a fully assembled distal resection guide assembly 140 is illustrated in FIG. 8, while its components are illustrated in FIGS. 6, 6A, 6B, and 7. The guide assembly 140 is composed of a suitable biocompatible material and includes a saw guide subassembly 142 and a capture subassembly 144, best illustrated in FIGS. 6, 6A, and 6B. The saw guide subassembly 142 includes a block 146. The block 146 includes a plurality of bone fastening-holes 147, a capture assembly attachment end 148, and a valgus angle adjustment end 150. The adjustment end 150 includes a plurality of positioning notches 152. Associated with the positioning notches 152 is a valgus angle scale 154 comprising a plurality of angle designations 156 engraved on the block 146. Use of the angle designations will be described below. Opposed to the outer side 158 of the block 146 is an inner anterior-surface abutment wall 160 shown in FIG. 8.

The block 146 includes a pair of saw guide arm supports 162 and 162' that pivotably support the saw guide arms 164 and 164' respectively. Relatedly, the capture subassembly 144 includes a pair of capture arms 166 and 166' which are mirror images of each other. Similarly, the saw guide arms 164 and 164' are mirror images of each other, as are the guide arm supports 162 and 162'. Accordingly, and to avoid unnecessary confusion, generally just one of any two like components of the invention will be discussed, although both the discussed component as well as the counterpart are generally shown in several figures, with the latter being identified by its being primed. It is to be understood that the discussion of the one will apply equally to the prime component not discussed.

The saw guide arm 164 includes a depending bone attachment plate 168 having a plurality of fastener holes 170. In addition, the saw guide arm 164 has fixed thereto a cylindrical member 172, as shown in FIG. 7. The cylindrical member 172 includes a threaded blind bore 174. The member 172 fits rotatably within a throughbore 176 formed in the block 146. A threaded fastener 178 is threaded into the threaded blind bore 174. The fastener 178 includes a head 180 which is positioned against a shoulder 182 formed in a counterbore 184 that is coaxial with the throughbore 176. This arrangement allows for rotatable movement of the arm 164 in relation to the block 146.

Subassembly 144 comprises the capture arms 166 and 166' and a center plate 186. The center plate 186 includes an upper surface 188 and a lower surface 190. A pair of opposed blade stop walls 192 and 192' (seen in shadow lines in FIG. 6A) are formed on the lower surface 190. The stop walls 192 and 192' limit movement of the saw blade (not shown).

The arms 166 and 166' are pivotably attached to the center plate 186 by a pair of fasteners 193 and 193'. The arms 166 and 166' respectively overlap the arms 164 and 164'. The subassembly 144 is removable as a single component from the subassembly 142. A center capture bolt 194 releasably holds the center plate 186 to the block 146 while an arm capture bolt 196 with a spacer 198 releasably holds the arm 166 to the arm 164. When the arm 166 is in place on the arm 164, it is spaced apart therefrom and is pivotable therewith, and a saw blade slot 200 is defined between the arms 164 and 166. It is through the slot 200 that a bone saw blade (not shown) is reciprocatingly moved.

The subassembly 144 is normally in its attached position as illustrated during and between surgeries and would ordinarily be removed only for cleaning or for maintenance. The arms 166 and 166' as well as the arms 164 and 164' are provided in different sizes to accommodate femurs of different diameters.

A distal condyle positioning shoe 202 is also provided and is removably attachable by a fastener 204 to the center plate 186. A threaded bore 205 is formed in the upper surface 188 for receiving the fastener 204. To verify correct alignment of the shoe 202 with respect to the center plate 186, a bore 207 is formed in the upper surface 188 for receiving an alignment pin 209 fitted to the shoe 202.

The shoe 202 includes a throughbore 206 which allows positioning of the shoe 202 over the center capture bolt 194. The positioning shoe 202 includes a pair of positioning fingers 208 and 208' that rest on the distal condyles. By resting on one or both of the condyles 36 and 36', the positioning shoe 202 dictates the depth of the cut of the distal resection.

To assure that the resection of the distal end of the femur 26 is made at a proper angle with respect to the long axis of the femur 26, a valgus guide subassembly 210 is provided and is removably attachable to the distal resection guide assembly 140. The valgus guide subassembly 210 includes a valgus guide arm 212 and a slide arm 214. The valgus guide arm 212 includes a slide arm attachment end 216 and an opposite positioning end 218. A knurled knob 220 is provided for engagement with an aperture 222 defined in the block 146 and releasably holds the valgus guide subassembly 210 to the assembly 140. The positioning end 218 includes a tooth 224 that is attached to the guide arm 212 by a cap screw 226. The guide arm 212 includes an axially defined channel 228 that houses a compression spring 230. The spring 230 acts on the tooth 224 to maintain its engagement in a desired position between adjacent notches 152. The spring 230, however, allows the operator to pull the tooth 224 from between the notches 152 for adjustment of the guide arm 212 with respect to the block 146.

The slide arm 214 comprises an intramedullary guide support portion 232 and an elongated connecting portion 234. A fastener 236 is provided at the slide arm attaching end 216 of the valgus guide arm 212 for attachment of the slide arm 214. The fastener 236 is fitted through an elongated slot 238 axially defined in the connecting portion 234. The elongated slot 238 allows for movement of the slide arm 214 with respect to the guide arm 212 as required for radial adjustment. The guide support portion 232 includes a tubular intramedullary retaining sleeve 240 having a rod-holding throughbore 242. The throughbore 242 allows passage of an intramedullary rod 244.

Positioning of the assembly 140 on the distal end of the femur 26 in preparation for the distal osteotomy is as follows. Prior to surgery, the valgus angle of the femur 26 is determined by the surgeon as is known in the art. The valgus guide subassembly 210 is adjusted to match the predetermined valgus angle by positioning the subassembly 210 so that the guide arm 212 is aligned with the selected valgus angle degree of the scale 154 engraved on the side 158 of the block 146. The tooth 224 is positioned between a pair of adjacent notches 152 defined in the block 146 to restrict movement of the subassembly 210 once in its selected position. For example, if the valgus angle of the patient's femur is 6° off-axis (which is very common), the arm 212 is rotated on the block 146 until it is aligned with the "6" on the scale 154.

The assembly 140, including the valgus guide subassembly 210, is fitted to the distal end of the femur 26 such that the interior-surface abutment wall 160 of the assembly block 146 is positioned flush against the resected anterior surface and the fingers 208 and 208' of the positioning shoe 202 are positioned to rest on the distal condyles 36 and 36' of the femur 26. In this position, it is to be understood that the assembly 140 is not movable in the anterior-posterior directions, but is movable in the medial-lateral directions. The medial-lateral rotation is, however, somewhat limited by the positioning shoe 202, but this limitation is not strict, and the fingers of the shoe 202 may be balanced off of one or both of the condyles. The shoe 202 need not to rest evenly on both of the condyles, but only on one, and such fitting nevertheless provides proper measurement of the amount of bone to be cut from the distal end of the femur 26.

Because the resection of the anterior femur fixes movement in one direction, it is the rotation of the assembly 140 that determines the angle of the distal cut with resect to the long axis of the femur 26. Accordingly, considerable care must be exercised when making the alignment. With the wall 160 of the assembly 140 positioned against the resected surface on the anterior distal end of the femur 26, the intramedullary rod 244 is positioned through the intramedullary retaining sleeve 240 and into the axial intramedullary rod hole 136.

With the rod 244 positioned in the hole 136, the arms 164 and 166 are positioned around the distal end such that the attachment plates 168 and 168' rest flush against the bone. Pins or screws (not shown) are then inserted into the bone through the holes 170 defined in the plate 168. Additionally, pins or screws (again not shown) are inserted into the interior cut side of the bone through holes 147 defined in the block 146. Once the assembly 140 is secured, the intramedullary rod 244 and the guide subassembly 210 are removed, and the surgeon resects the distal end of the femur 26 by using a bone saw (not shown) through the slot 200. After the selected amount of bone has been cut away, the guide assembly 140 is removed, and the distal osteotomy is complete.

Three other resections remain to be made on the distal end of the femur 26, and these include a posterior resection, a chamfer cut between the resected distal surface and the resected posterior surface, and a chamfer cut between the resected distal surface and the resected anterior surface. A compound posterior femur-chamfer resection guide assembly, generally illustrated as 246 and shown in FIGS. 9, 9A, 9B, 9C, 9D, and 10, is provided for this purpose. The compound assembly 246 comprises a body 248 having a distal end contacting portion 250, an anterior cut contacting portion 252, and a posterior cut guide portion 254. When the compound assembly 246 is in its resection position as illustrated in FIG. 10, the inner, bone-facing wall of the anterior cut contacting portion 252 rests flush against the resected anterior surface, while the inner, bone-facing wall of the distal end contacting portion 250 rests flush against the resected distal surface.

The distal end contacting portion 250 is connected to the anterior cut contacting portion 252 by a pair of arms 256 and 256', seen in FIGS. 9 and 9B The portions 250 and 252 and the arms 256 and 256' define a window 258 through which extends a portions of the distal end to be cut, as illustrated in FIG. 10 and as identified "A". Externally, the pair of arms 256 and 256' provide a pair of coplanar cutting surfaces 260 and 260' against which a bone saw blade (not shown) may be guided for making the anterior-distal chamfered cut.

The posterior cut guide portion 254 includes a posterior cut guide 262. The guide 262 provides a surface against which a bone saw blade (not shown) is positioned while the posterior cut is being made. To provide a method by which greater cutting accuracy may be obtained, a capture plate 264 is optionally provided and is removably attached to the guide 262 by a threaded fastener 266. A threaded bore 267 is formed in the posterior cut portion 254 for receiving the fastener 266. To verify that the capture plate 264 is properly positioned, a smooth bore 269 is also formed in the posterior cut portion 254 for receiving an alignment pin 271 fixed to the capture plate 264. When the capture plate 264 is fitted to the guide 262, a saw blade space 268 is defined that is wide enough to allow passage of a saw blade, but is narrow such that lateral movement of the blade is restricted.

Adjacent the guide 262 are a pair of collinear chamfer slots 270 and 270', best shown in FIGS. 9 and 9B The chamfer slots 270 and 270' provide the surgeon with a guide by which the posterior-distal chamfer may be accurately made.

Use of the compound assembly 246 is as follows. The compound assembly 246 is positioned on the femur 26 having resected anterior and distal surfaces. The inner, bone-facing wall of the anterior cut contacting portion 252 is snugly fitted against the resected anterior surface and the inner, bone-facing wall of the distal end contacting portion 250 is snugly fitted against the resected distal surface. Temporary fasteners, such as pins or screws (not shown), are fitted through the holes 272 and 272' of the anterior cut contacting portion 252 and through at least two of the holes 274, 274', 276, or 276' of the posterior cut guide portion 254. (The plurality of holes is provided to allow the surgeon to select the best point of attachment.) Thus secured, the surgeon is able to accurately make the anterior-distal chamfer resection, the posterior resection, and the posterior-distal chamfer resection. Once the resections are complete, the compound assembly 246 is removed. With the five resections thus made, the distal end of the femur 26 must be altered in additional known ways (e.g., axial reaming) to receive the femoral component 22, which is thereafter attached in a conventional and known manner.

Figure 12:
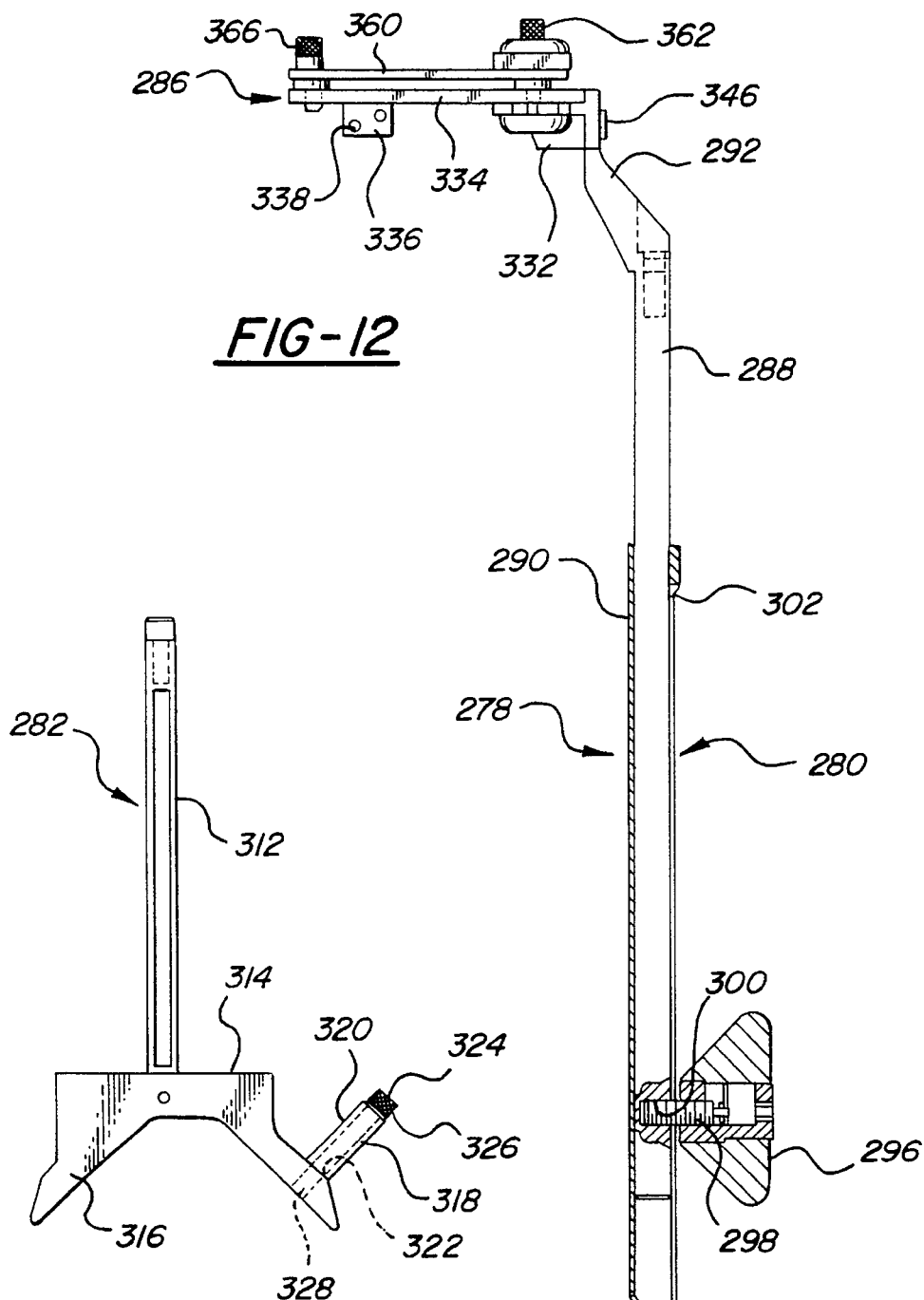
FIG. 12 is an elevational side view of a tibia resection guide assembly according to the present invention.
Figure 12A:
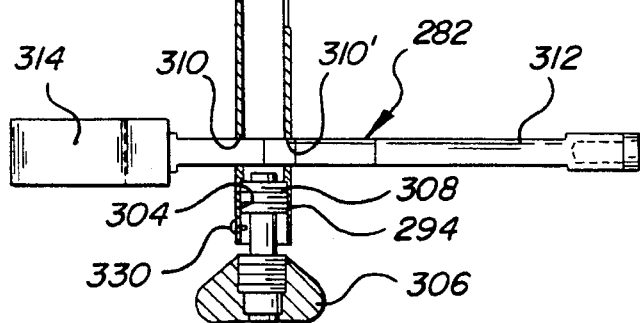
FIG. 12A is a top plan view of the ankle alignment subassembly for attachment to the tibia resection guide assembly of the present invention.
Figure 13:
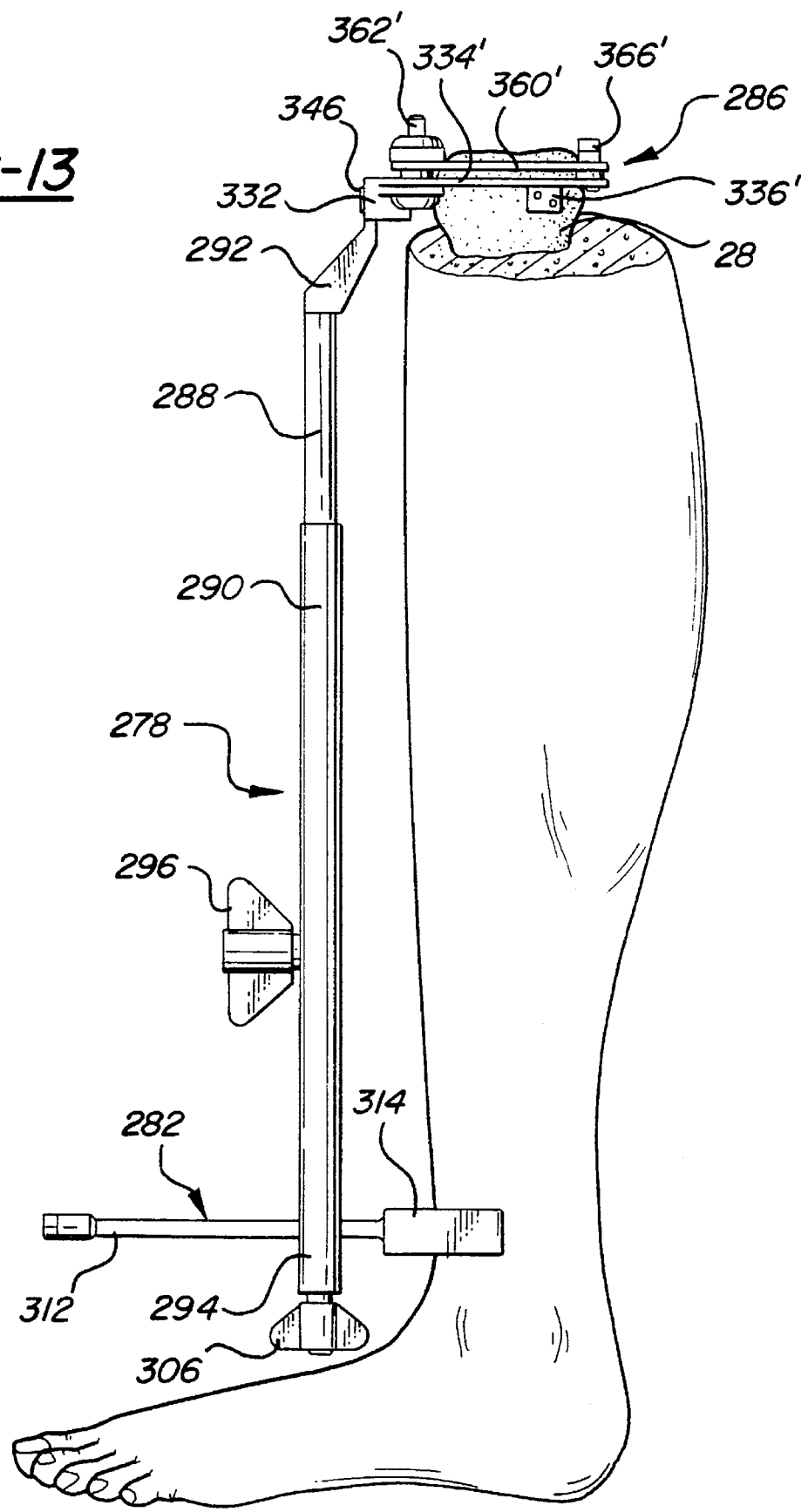
FIG. 13 is a side elevational view illustrating the placement of the tibia resection guide assembly in position for a proximal tibia osteotomy.

Preparation of the tibia 28 to receive the tibial component 24 initially involves the cutting of the proximal end of the bone. Only one surface resection is made to receive the component 24. A tibia resection guide assembly, generally indicated as 278 in FIGS. 12 and 13, is provided for this purpose. The tibia resection guide assembly 278 includes an elongated and adjustable shaft subassembly 280, an ankle alignment subassembly 282, a capture plate subassembly 284, and a saw guide subassembly 286, the latter being best shown in FIGS. 11, 11A, 11B, and 11C.

The shaft subassembly 280 includes an inner shaft 288 and an external sleeve 290. The assembly 280 further includes an ankle alignment subassembly attachment end 292 and a saw guide subassembly attachment end 294.

The inner shaft 288 is axially movable within the external sleeve 290 so that the length of the shaft subassembly 280 may be altered to accommodate tibias of different lengths. A locking wing nut 296 is threaded onto a threaded stud 298. The threaded stud 298 is threaded into a bore 300 formed in the inner shaft 288. An axial slot 302 is defined along the external sleeve 290 and is provided to allow movement of the threaded stud 298 as the shaft 288 is adjusted in and out of the sleeve 290. Rotation of the wing nut 296 in a first direction locks a portion of the external sleeve 290 between the shaft 288 and the wing nut 296. Rotation of the wing nut 296 in a second direction opposite the first direction releases the shaft 288 for axial adjustment.

The ankle alignment subassembly attachment end 292 of the shaft subassembly 280 includes a threaded bore 304. A wing nut 306 includes a threaded end 308 that is threadably mated to the threaded bore 304. A pair of opposed and aligned holes 310 and 310' are formed in the sleeve 290.

The ankle alignment subassembly 282 includes an elongated rod 312 and an ankle brace 314. The brace 314 includes a generally U-shaped body 316 and a fine adjustment assembly 318 having a tubular body 320 with a threaded throughbore 322 and an adjusting screw 324. The screw 324 comprises a knob 326 and a threaded shaft 328.

The elongated rod 312 of the subassembly 282 is movable perpendicularly with respect to the shaft subassembly 280 and is fitted through the pair of opposed and aligned holes 310 and 310'. The rod 312 is locked in place against movement by selective rotation of the wing nut 306. Rotation of the wing nut 306 in a first direction locks the rod 312 against movement by moving the threaded end 308 into engagement with the adjacent portion of the rod 312, thus pressing a portion of the rod 312 opposite the threaded end 308 of the wing nut 306 against adjacent walls of the holes 310 and 310'. Movement of the wing nut 306 in a second direction opposite the first direction releases the rod 312 for adjustment or disassembly. A stud 312 prevents disconnection of the wing nut 306 from the assembly 280 upon excessive rotation of the wing nut 306 in the second direction.

The saw guide subassembly 286 and the capture plate subassembly 284 are similar in design and function to saw guides and capture plate subassemblies discussed above with respect to the assembly 140. As the description above with respect to the assembly 140, only one of any two like components of the subassemblies 286 and 284 will be discussed, although both the discussed component as well as its primed counterpart are generally shown in several figures. It is again to be understood that discussion of the one will apply equally to the primed component not discussed.

The saw guide subassembly 286 includes a central block 332 and a saw guide swing arm 334 having a fastening plate 336 depending therefrom. The plate 336 includes apertures 338 through which are positioned removable fasteners such as pins or screws (not shown). The central block 332 includes a rod attaching side 340 and an arcuate tibia-contacting side 342. The rod attaching side 340 has a slot 344 formed into which is fitted the attachment end 292 of the shaft subassembly 280. The end 292 is fixed to the block 332 by a fastener 346 which is mated with a throughbore 348 formed in the block 332. A plurality of attachment throughbores 350 are formed through the block 332.

The block 332 includes a pair of opposed arm supports 352 and 352'. The saw guide swing arm 334 includes a cylindrical formation 354 that is rotatably engaged with an aperture 356 formed in the arm support 352.

The saw capture plate subassembly 284 includes a central plate 358 and a capture plate swing arm 360. Between the central plate 358 and the central block 332 is defined a saw blade slot 361 which constrains a saw blade (not shown) during resection. The swing arm 360 is rotatably attached to the central plate 358 by a fastener 346 having a fastening end (not shown) that is releasably mated with an aperture 364 defined in the swing arm 334, as shown in FIG. 11A. The capture plate swing arm 360 also includes an end fastener 366 having a fastening end (not shown) that is releasably mated with an aperture 368 defined in the end of the swing arm 334 opposite the aperture 364. As with the arms 164 and 166 of the assembly 140, the arms 334 and 360 may be of different lengths to accommodate tibias of different diameters.

In operation, the capture plate subassembly 284 is attached to the saw guide subassembly 286 using the fasteners 346 and 366 and is left in this position and generally remains in this position during in between procedures, although it may be selectively removed for cleaning and maintenance. The arms 334 and 360 are in spaced apart relation from one another, and therefore define between them a saw blade passing space 370. The wing nut 296 is rotated in the second direction to allow the shaft 288 to be adjusted within the sleeve 290 to a preferred length as dictated by the length of the lower leg of the patient. Once proper length is determined, the wing nut 296 is rotated in its first direction and the shaft 288 is locked against further axial movement within the sleeve 290. The ankle alignment subassembly 282 is also adjusted to its correct position after the wing nut 306 is rotated in its second direction to allow movement of the rod 312 through the sleeve 290, and the assembly 278 is positioned against the leg as generally shown in FIG. 13. Fine adjustment with respect to the ankle is made upon rotation of the adjusting screw 324.

Once the correct adjustment of the subassembly 282 is determined, the wing nut 306 is rotated in its first direction to lock the rod 312 against further movement. The swing arms 334 and 360 are then swung into position as a unit against the proximal end of the tibia 28 such that the plate 336 rests substantially flush against the side of the bone. In its position, temporary fasteners such as pins or screws (not shown) are fitted through the apertures 338. Similarly, the same types of temporary fasteners are fitted through the throughbores 350 formed in the block 332. The swing arm and block fasteners hold the subassemblies 284 and 286 against movement. Thus fixed, the surgeon positions a bone saw blade in the space 370 formed between the swing arms 334 and 360 and resects the proximal end of the tibia 28. Reciprocal movement of the saw blade through the space 370 resects the bone. The assembly 278 is thereafter removed.

After the proximal end of the tibia 28 has been resected, the tibia must be further altered in known ways (e.g., axial reaming) to receive the tibial component 24 which is thereafter attached in a conventional and known manner.

Those skilled in the art can now appreciate from the foregoing description that the broad teachings of the present invention can be implemented in a variety of forms. Therefore, while this invention has been described in connection with particular examples thereof, the true scope of the invention should not be so limited since other modifications will become apparent to the skilled practitioner upon a study of the drawings, specification and following claims.

What is claimed is:

1. A surgical instrument for resecting a bone with a saw, the saw including a blade, said surgical instrument comprising:
   a guide body operable to be used during resection of the bone; and
   a laterally extending member defined by a first component operably attached to said guide body at a first attachment area and a second component operably attached to said guide body at a second attachment area, said attachment areas defining two opposing walls, said components being spaced apart such that a constrained opening is defined therebetween for capturing the blade, said constrained opening extending substantially between said attachment areas.

2. The surgical instrument of claim 1, wherein said first component defines a saw blade-positioning swing arm, said swing arm being removably attachable to said guide body and being pivotable with respect thereto.

3. The surgical instrument of claim 2, wherein said second component defines a saw blade capture plate, said capture plate substantially overlapping said saw blade-positioning swing arm.

4. The surgical instrument of claim 2, wherein said swing arm comprises a first swing arm having a first length and wherein said surgical instrument includes a second swing arm having a second length, said first length and said second length being different, said first swing arm being interchangeable with said second swing arm.

5. The surgical instrument of claim 4, wherein said first swing arm includes a first capture plate substantially overlapping said first swing arm in spaced apart relation therefrom such that a first constrained opening is defined therebetween for capturing the blade.

6. The surgical instrument of claim 5, wherein said second swing arm includes a second capture plate substantially overlapping said first swing arm in spaced apart relation therefrom such that a second constrained opening is defined therebetween for capturing the blade.

7. The surgical instrument of claim 1, wherein the bone to be resected has a long axis, said guide body further including an alignment member attached thereto for aligning said surgical instrument with respect to the long axis of the bone.

8. The surgical instrument of claim 1, said guide body further including means for releasably attaching said surgical instrument to the bone.

9. The surgical instrument of claim 2, wherein the bone to be resected is a femur and said guide body further includes a distal femur contacting surface for positioning said instrument against the distal end of the femur, whereby said swing arm is positionable partially around the anterior portion of the distal femur.

10. A method for resecting a bone with a saw, the saw including a blade and the bone having a long axis, said method comprising the steps of:
   providing a surgical instrument for resecting the bone, said surgical instrument having a guide body and a laterally extending member operably attached to said guide body, said laterally extending member defined by a first component operably attached to said guide body at a first attachment area and a second component operably attached to said guide body at a second attachment area, said attachment areas defining two opposing walls, said components being spaced apart such that a constrained opening is defined therebetween for capturing the blade, said constrained opening extending substantially between said attachment areas, said surgical instrument further including an alignment member attached to said guide body for aligning said surgical instrument with respect to the long axis of the bone, said laterally extending member including a constrained opening through which the blade is able to pass;
   positioning said guide body into axial alignment with the long axis of the bone by observing the relative position of said alignment member;
   moving said laterally extending member from a first position in which said laterally extending member is spaced apart from the bone to a second position in which at least a portion of said laterally extending member is located adjacent to the bone;
   inserting the blade through said constrained opening formed between said attachment areas; and
   resecting the bone by movement of the blade of the saw.

11. The method for resecting a bone of claim 10, wherein said surgical instrument defines an anterior femur resection guide assembly and said constrained opening defines an anterior femur resection guide assembly constrained opening, said step of positioning said guide body including the step of positioning said anterior femur resection guide assembly against the distal end of a femur, said step of moving said laterally extending member including the step of moving said laterally extending member to a position adjacent the femur, said step of inserting the saw blade through the constrained opening including the step of inserting the saw blade through said anterior femur resection guide assembly constrained opening, and said step of resecting the bone including the step of shaping the anterior side of the distal end of the femur to form a resected anterior surface.

* * * * *